(12) United States Patent
Prandi et al.

(10) Patent No.: US 9,078,713 B2
(45) Date of Patent: *Jul. 14, 2015

(54) ORTHOPEDIC IMPLANT IN THE FORM OF A PLATE TO BE FIXED BETWEEN TWO BONE PARTS

(71) Applicant: MEMOMETAL TECHNOLOGIES, Bruz (FR)

(72) Inventors: Bernard Prandi, Rennes (FR); Keith Wapner, Philadelphia, PA (US); Charles P. Wapner, Media, PA (US); Peter W. Wapner, Media, PA (US)

(73) Assignee: MEMOMETAL TECHNOLOGIES (FR)

( * ) Notice: Subject to any disclaimer, the term of this patent is extended or adjusted under 35 U.S.C. 154(b) by 88 days.

This patent is subject to a terminal disclaimer.

(21) Appl. No.: 14/041,706

(22) Filed: Sep. 30, 2013

(65) Prior Publication Data

US 2014/0052193 A1 Feb. 20, 2014

Related U.S. Application Data

(63) Continuation of application No. 12/918,071, filed as application No. PCT/FR2009/051879 on Oct. 2, 2009, now Pat. No. 8,556,946.

(30) Foreign Application Priority Data

Oct. 2, 2008 (FR) .................................. 08 56694

(51) Int. Cl.
*A61B 17/80* (2006.01)
*A61B 17/84* (2006.01)

(52) U.S. Cl.
CPC ......... *A61B 17/8061* (2013.01); *A61B 17/8004* (2013.01); *A61B 17/808* (2013.01); *A61B 17/8057* (2013.01); *A61B 17/846* (2013.01); *A61B 17/809* (2013.01)

(58) Field of Classification Search
CPC .. A61B 17/80; A61B 17/808; A61B 17/8057; A61B 17/8061
USPC ............................ 606/60, 280–299, 300–331
See application file for complete search history.

(56) References Cited

U.S. PATENT DOCUMENTS 2,486,303 A 10/1949 Longfellow
3,528,085 A 9/1970 Reynolds
(Continued)

FOREIGN PATENT DOCUMENTS

DE 3027148 A1 12/1981
DE 8227727 U1 12/1982
(Continued)

OTHER PUBLICATIONS

Catalogue General 1987-1988, plaques d'osteosynthese, bone plates, Division of Pfzer Hospital Products Group, Bagneux, France.
(Continued)

*Primary Examiner* — Christopher Beccia
(74) *Attorney, Agent, or Firm* — Lerner, David, Littenberg, Krumholz & Mentlik, LLP

(57) ABSTRACT

The invention relates to a plate fixed between two bone parts by way of screws engaged in holes formed in the thickness of said plate. The plate comprises an angled member or rib which is inclined according to an angle of between about 30° and 60° in relation to the plane defined by the plate. The angled member or rib has a hole for engaging a screw and is located in the central part of the width, over a determined part of the length of the plate, so that the screw brings the two bone parts into a compressive position.

40 Claims, 2 Drawing Sheets

(56) References Cited

U.S. PATENT DOCUMENTS

| | | | |
|---|---|---|---|
| 3,534,731 A | 10/1970 | Muller | |
| 3,552,389 A | 1/1971 | Allgower et al. | |
| 3,779,240 A | 12/1973 | Kondo | |
| RE28,841 E | 6/1976 | Allgower et al. | |
| 4,388,921 A | 6/1983 | Sutter et al. | |
| 4,408,601 A | 10/1983 | Wenk | |
| RE31,628 E | 7/1984 | Allgower et al. | |
| 4,493,317 A | 1/1985 | Klaue | |
| 4,503,737 A | 3/1985 | DiGiovanni | |
| 4,513,744 A | 4/1985 | Klaue | |
| 4,651,724 A | 3/1987 | Berentey et al. | |
| 4,800,874 A | 1/1989 | David et al. | |
| 4,957,496 A | 9/1990 | Schmidt | |
| 4,988,350 A * | 1/1991 | Herzberg | 606/65 |
| 5,105,690 A | 4/1992 | Lazzara et al. | |
| 5,304,180 A | 4/1994 | Slocum | |
| 5,347,894 A | 9/1994 | Fischer | |
| 5,487,741 A | 1/1996 | Maruyama et al. | |
| 5,662,655 A | 9/1997 | Laboureau et al. | |
| 5,667,510 A | 9/1997 | Combs | |
| 5,674,222 A | 10/1997 | Berger et al. | |
| 5,709,686 A | 1/1998 | Talos et al. | |
| 5,810,822 A | 9/1998 | Mortier | |
| 5,827,285 A | 10/1998 | Bramlet | |
| 5,853,413 A | 12/1998 | Carter et al. | |
| 5,904,684 A | 5/1999 | Rooks | |
| 5,931,839 A | 8/1999 | Medoff | |
| 6,146,382 A | 11/2000 | Hurlbert | |
| 6,183,475 B1 | 2/2001 | Lester et al. | |
| 6,348,052 B1 | 2/2002 | Sammarco | |
| 6,379,359 B1 | 4/2002 | Dahners | |
| 6,383,186 B1 | 5/2002 | Michelson | |
| 6,533,786 B1 | 3/2003 | Needham et al. | |
| 6,544,266 B1 | 4/2003 | Roger et al. | |
| 6,565,570 B2 | 5/2003 | Sterett et al. | |
| 6,576,018 B1 | 6/2003 | Holt | |
| 6,623,486 B1 | 9/2003 | Weaver et al. | |
| 6,626,907 B2 | 9/2003 | Campbell et al. | |
| 6,669,700 B1 | 12/2003 | Farris et al. | |
| 6,669,701 B2 | 12/2003 | Steiner et al. | |
| 6,692,503 B2 | 2/2004 | Foley et al. | |
| 6,712,820 B2 | 3/2004 | Orbay | |
| 6,719,759 B2 | 4/2004 | Wagner et al. | |
| 6,730,091 B1 | 5/2004 | Pfefferle et al. | |
| 6,764,489 B2 | 7/2004 | Ferree | |
| 6,960,211 B1 | 11/2005 | Pfefferle et al. | |
| 7,037,342 B2 | 5/2006 | Nilsson et al. | |
| 7,044,951 B2 * | 5/2006 | Medoff et al. | 606/71 |
| 7,108,697 B2 | 9/2006 | Mingozzi et al. | |
| 7,137,987 B2 | 11/2006 | Patterson et al. | |
| 7,179,260 B2 * | 2/2007 | Gerlach et al. | 606/291 |
| 7,326,218 B2 | 2/2008 | Sterett et al. | |
| 7,341,589 B2 | 3/2008 | Weaver et al. | |
| 7,344,538 B2 | 3/2008 | Myerson et al. | |
| D587,370 S | 2/2009 | Coillard-Lavirotte et al. | |
| 7,491,220 B2 | 2/2009 | Coughln | |
| D596,294 S | 7/2009 | Coillard-Lavirotte et al. | |
| 7,695,472 B2 | 4/2010 | Young | |
| 7,766,948 B1 | 8/2010 | Leung | |
| 7,771,457 B2 | 8/2010 | Kay et al. | |
| D623,745 S | 9/2010 | Kay et al. | |
| 7,799,061 B2 | 9/2010 | Kay et al. | |
| 7,819,903 B2 | 10/2010 | Fraser et al. | |
| 7,857,836 B2 | 12/2010 | Huebner et al. | |
| 7,931,680 B2 | 4/2011 | Myerson et al. | |
| 8,080,010 B2 | 12/2011 | Schulz et al. | |
| 8,100,954 B2 | 1/2012 | Kay et al. | |
| 8,100,983 B2 | 1/2012 | Schulte | |
| 8,852,246 B2 * | 10/2014 | Hansson | 606/286 |
| 2001/0011172 A1 | 8/2001 | Orbay et al. | |
| 2001/0047172 A1 | 11/2001 | Foley et al. | |
| 2002/0045901 A1 | 4/2002 | Wagner et al. | |
| 2002/0183752 A1 | 12/2002 | Steiner et al. | |
| 2003/0040748 A1 * | 2/2003 | Aikins et al. | 606/70 |
| 2003/0060827 A1 | 3/2003 | Coughlin | |
| 2003/0195516 A1 | 10/2003 | Sterett et al. | |
| 2003/0199875 A1 | 10/2003 | Mingozzi et al. | |
| 2004/0059334 A1 | 3/2004 | Weaver et al. | |
| 2004/0092929 A1 | 5/2004 | Zindrick | |
| 2004/0093081 A1 | 5/2004 | Nilsson et al. | |
| 2004/0097950 A1 | 5/2004 | Foley et al. | |
| 2004/0167522 A1 | 8/2004 | Niederberger et al. | |
| 2004/0172028 A1 | 9/2004 | Roger | |
| 2004/0181228 A1 | 9/2004 | Wagner et al. | |
| 2004/0186477 A1 | 9/2004 | Winquist et al. | |
| 2004/0210234 A1 | 10/2004 | Coillard-Lavirotte et al. | |
| 2004/0214137 A1 | 10/2004 | Walton | |
| 2004/0236332 A1 | 11/2004 | Frigg | |
| 2005/0015089 A1 | 1/2005 | Young et al. | |
| 2005/0070904 A1 | 3/2005 | Gerlach et al. | |
| 2005/0080421 A1 | 4/2005 | Weaver et al. | |
| 2005/0085913 A1 | 4/2005 | Fraser et al. | |
| 2005/0090825 A1 | 4/2005 | Pfefferle et al. | |
| 2005/0171544 A1 * | 8/2005 | Falkner | 606/69 |
| 2005/0182408 A1 | 8/2005 | Pfefferle et al. | |
| 2005/0277937 A1 | 12/2005 | Leung et al. | |
| 2005/0277941 A1 | 12/2005 | Trumble et al. | |
| 2006/0004362 A1 | 1/2006 | Patterson et al. | |
| 2006/0015102 A1 | 1/2006 | Toullec et al. | |
| 2006/0058796 A1 | 3/2006 | Hartdegen et al. | |
| 2006/0106387 A1 | 5/2006 | Fanger et al. | |
| 2006/0149261 A1 | 7/2006 | Nilsson et al. | |
| 2006/0173459 A1 | 8/2006 | Kay et al. | |
| 2006/0200145 A1 | 9/2006 | Kay et al. | |
| 2006/0235397 A1 | 10/2006 | Sanders et al. | |
| 2006/0241607 A1 | 10/2006 | Myerson et al. | |
| 2006/0241608 A1 | 10/2006 | Myerson et al. | |
| 2006/0241609 A1 | 10/2006 | Myerson et al. | |
| 2007/0142920 A1 | 6/2007 | Niemi | |
| 2007/0233106 A1 | 10/2007 | Horan et al. | |
| 2007/0270850 A1 | 11/2007 | Geissler | |
| 2008/0015593 A1 | 1/2008 | Pfefferle et al. | |
| 2008/0051791 A1 | 2/2008 | Young et al. | |
| 2008/0091197 A1 | 4/2008 | Coughlin | |
| 2008/0114360 A1 | 5/2008 | Da Frota Carrera | |
| 2008/0132960 A1 | 6/2008 | Weaver et al. | |
| 2008/0161860 A1 | 7/2008 | Ahrens et al. | |
| 2008/0208262 A1 | 8/2008 | Butler et al. | |
| 2008/0249572 A1 * | 10/2008 | Tandon | 606/280 |
| 2008/0249573 A1 | 10/2008 | Buhren et al. | |
| 2009/0024173 A1 | 1/2009 | Reis, Jr. | |
| 2009/0036933 A1 | 2/2009 | Dube et al. | |
| 2009/0093849 A1 | 4/2009 | Grabowski | |
| 2009/0118769 A1 | 5/2009 | Sixto, Jr. et al. | |
| 2009/0198285 A1 | 8/2009 | Raven, III | |
| 2009/0210010 A1 | 8/2009 | Strnad et al. | |
| 2009/0210011 A1 | 8/2009 | Den Hartog et al. | |
| 2009/0210013 A1 | 8/2009 | Kay et al. | |
| 2009/0228048 A1 | 9/2009 | Duncan et al. | |
| 2009/0234359 A1 | 9/2009 | Onoue et al. | |
| 2009/0275987 A1 | 11/2009 | Graham et al. | |
| 2009/0306724 A1 | 12/2009 | Leither et al. | |
| 2009/0312759 A1 | 12/2009 | Ducharme et al. | |
| 2010/0016900 A1 | 1/2010 | Terres et al. | |
| 2010/0057214 A1 | 3/2010 | Graham et al. | |
| 2010/0121324 A1 | 5/2010 | Tyber et al. | |
| 2010/0121325 A1 | 5/2010 | Tyber et al. | |
| 2010/0125300 A1 | 5/2010 | Blitz et al. | |
| 2010/0160973 A1 | 6/2010 | Leung | |
| 2010/0217328 A1 | 8/2010 | Terrill et al. | |
| 2010/0256638 A1 | 10/2010 | Tyber et al. | |
| 2010/0256639 A1 | 10/2010 | Tyber et al. | |
| 2010/0274293 A1 | 10/2010 | Terrill et al. | |
| 2010/0305618 A1 | 12/2010 | Kay et al. | |
| 2010/0324556 A1 | 12/2010 | Tyber et al. | |
| 2011/0004253 A1 | 1/2011 | Fraser et al. | |
| 2011/0009866 A1 | 1/2011 | Johnson et al. | |
| 2011/0087229 A1 | 4/2011 | Kubiak et al. | |
| 2011/0087295 A1 | 4/2011 | Kubiak et al. | |
| 2011/0092981 A1 | 4/2011 | Ng et al. | |
| 2011/0093017 A1 | 4/2011 | Prasad et al. | |
| 2011/0093018 A1 | 4/2011 | Prasad et al. | |
| 2011/0118739 A1 | 5/2011 | Tyber et al. | |
| 2011/0125153 A1 | 5/2011 | Tyber et al. | |

(56) References Cited

U.S. PATENT DOCUMENTS

| | | |
|---|---|---|
| 2011/0213367 A1 | 9/2011 | Tyber et al. |
| 2011/0218535 A1 | 9/2011 | Wang et al. |
| 2011/0230884 A1 | 9/2011 | Mantzaris et al. |
| 2011/0264148 A1 | 10/2011 | Prandi et al. |
| 2011/0306976 A1 | 12/2011 | Kubiak et al. |
| 2011/0306977 A1 | 12/2011 | Michel et al. |

FOREIGN PATENT DOCUMENTS

| | | |
|---|---|---|
| DE | 3630862 A1 | 3/1988 |
| EP | 0 705 572 A2 | 4/1996 |
| EP | 1707227 A2 | 10/2006 |
| EP | 1897509 A1 | 3/2008 |
| FR | 590290 B | 3/1925 |
| FR | 590290 A | 6/1925 |
| FR | 2362616 A1 | 3/1978 |
| FR | 2764183 A1 | 12/1998 |
| FR | 2846870 A1 | 5/2004 |
| FR | 2912895 A1 | 8/2008 |
| WO | 9516403 A1 | 6/1995 |
| WO | 9528887 A1 | 11/1995 |
| WO | 9605778 A1 | 2/1996 |
| WO | 02098306 A1 | 12/2002 |
| WO | 2007131287 A1 | 11/2007 |

OTHER PUBLICATIONS

Manual of Small Animal Fracture Repair and Management, Jan. 1, 1998, pp. 80-81.
Vitallium Screw-Plate-Systems of Prof. R. Judet, 12 pages, 1974, Howmedica International, Inc. Shannon Industrial Estate, Co. Clare, Ireland.

* cited by examiner

ORTHOPEDIC IMPLANT IN THE FORM OF A PLATE TO BE FIXED BETWEEN TWO BONE PARTS

CROSS-REFERENCE TO RELATED APPLICATIONS

This application is a continuation of U.S. application Ser. No. 12/918,071, filed on Oct. 29, 2010, which is a national phase entry under 35 U.S.C. §371 of International Application No. PCT/FR2009/051879, filed Oct. 2, 2009, published in French, which claims priority from French Patent Application No. 0856694, filed Oct. 2, 2008, all of which are incorporated herein by reference in their entireties.

BACKGROUND OF THE INVENTION

The invention relates to the technical field of orthopedic implants.

More particularly, the invention relates to a plate for arthrodesis or osteosynthesis adapted to be fixed between two bone parts.

In a manner known to one having ordinary skill in the art, this type of plate generally has holes for engaging screws, allowing arthrodesis between two bones or osteosynthesis between two bone fragments. This is, for example, the case for bones of the hand or foot, without however excluding other applications, particularly in the field of the spine. Depending on the pathology to be treated, these plates can have a general rectilinear or other geometric shapes.

From this state of the art, one of the objects the invention proposes to attain is to improve, in a sure and efficient manner, compression in a precise direction between the bone parts subjected to the plate.

To attain the given object to enhance the compression between the two relative bone parts, according to the invention, the plate has a formation that orients at least one screw at an angle with respect to a plane defined by the plate, the angle being between about 30° and 60°.

According to an advantageous embodiment, the formation is a tab that is angled according to an angle between 30° and 60°, and having a hole for engaging the screw. The angled tab results from a cut out and a deformation of a portion of the plate.

In another embodiment, the formation is a hole angled at an angle between 30° and 60° for engaging the screw.

Considering the problem to be solved, the formation is located on a determined portion of the length of the plate so that the screw ensures the compression of the two bone parts.

BRIEF DESCRIPTION OF THE DRAWINGS

The invention is described hereinafter in more detail, with reference to the attached drawings in which.

DETAILED DESCRIPTION

Figure 1:
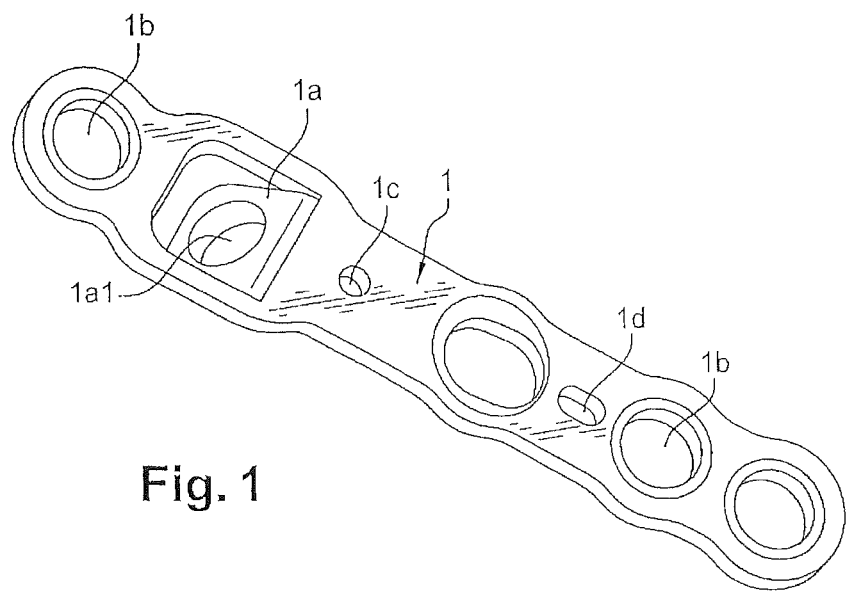
FIG. 1 is a perspective view of an embodiment of the plate.
Figure 2:
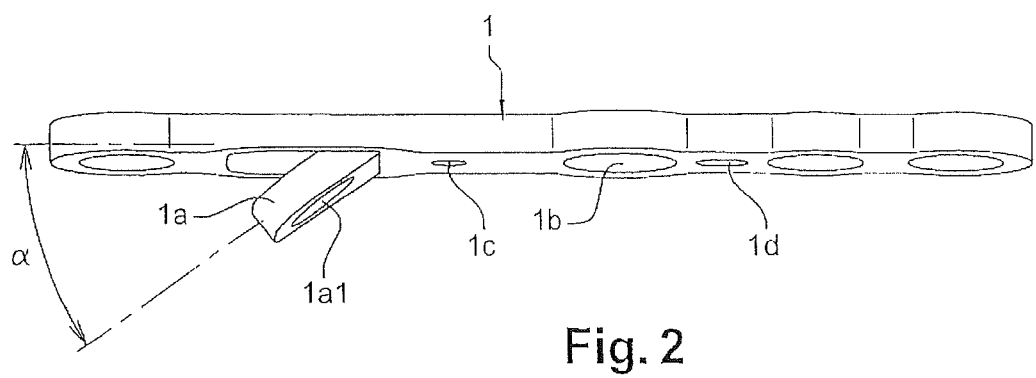
FIG. 2 is a side view of the plate.

According to the invention, the plate 1 has at least one formation 1a adapted to enable the positioning of at least one screw 2, at an angle α of between 30° and 60° with respect to a plane of the plate (FIG. 2).

In one embodiment, the formation 1a is an angled tab cut out and deformed from the plate. For example, the deformation is made with a cutting-punching operation. This angled tab has a hole 1a1 for screw 2. The angled tab 1a is positioned along the length of the plate so that after the screw 2 is fitted to it, the screw ensures the compression together of the two bone parts, as indicated below in the description.

In another embodiment, to allow for an angular orientation of the screw 2 according to an angle between about 30° and 60°, the formation 1a can be formed as an angled hole. It must be noted that the tab 1a enables adaptation of the angle as a function of the pathology to be treated, given that it is possible to deform this tab at will. In other words, the angle can be adjusted over a few degrees directly by the surgeon in the operating room, using an appropriate tool.

Figure 3:
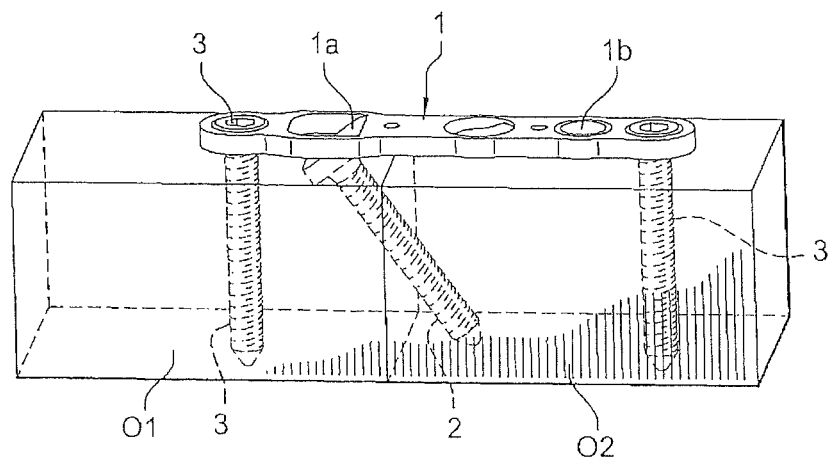
FIGS. 3 and 4 are perspective views showing the mounting of the plate between two bone parts and their orientation by means of the plate according to the invention, the bone parts being shown schematically.
Figure 4:
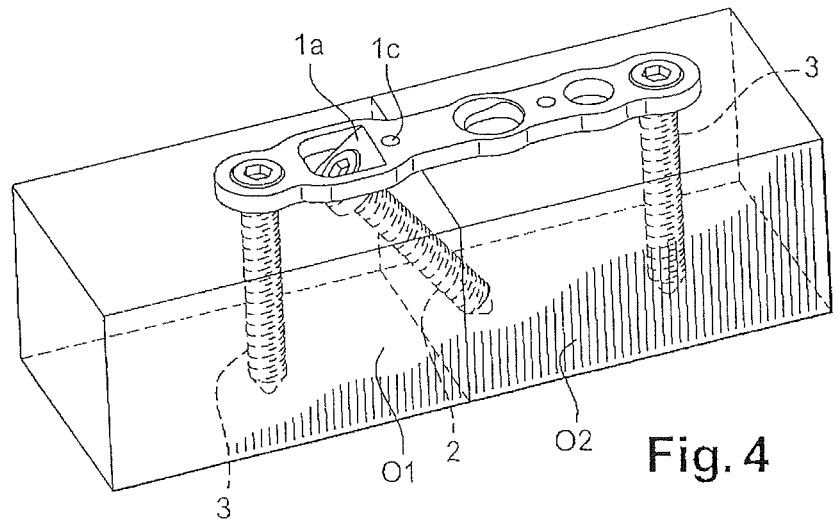

With reference to FIGS. 3 and 4 that show the positioning of the plate 1 between two bone parts O1 and O2:

Once the osteotomies have been carried out, a template of the plate, which does not have a guide formation, enables the position of the tab to be determined.

After determining the position of the tab, the surgeon makes a corresponding recess with the appropriate rasp.

Once the plate having the tab has been positioned, the surgeon sets one or two screws 3, on a side of the site of the osteosynthesis or the arthrodesis toward the tab. A temporary fastening pin can, possibly, be positioned in a complementary lug.

The screw 2 is then engaged in the hole 1a1 of the tab 1a to place the fracture in compression.

Once the compression has been done, the surgeon can screw one or several other additional fastening screws 3 and remove the temporary pin.

In a known manner, this plate 1 has smooth and/or threaded holes for the fastening screws 3 set in the bone parts O1 and O2 to engage in, as shown in FIGS. 3 and 4.

Similarly, the plate 1 can have at least one hole 1c for a pin for temporarily positioning the plate 1. Advantageously, the plate 1 can have a guide 1c for the insertion of a pin on the side of one of the bone parts O1 and another guide 1d for the insertion of another pin on the side of the other bone part O2.

Considering the effect of the desired compression, such as indicated above, the guide 1c is a circular hole whose diameter corresponds substantially to that of the pin, whereas the other guide 1d can be an elongated slot.

These provisions thus enable the bone to slide under the plate 1 as the screws are set, while ensuring compression along a precise direction, generally axially or parallel to the plate. The pins are of any known and appropriate type, and perfectly known to one having ordinary skill in the art.

The plate 1 can have several shapes, so that the holes 1a in particular can be aligned or arrayed, all or in part, according to the corners of a triangle or of a quadrilateral. These provisions, in triangle or in quadrilateral, of the screws, improve the stability of the mounting.

It must be noted also that the plate 1, no matter its shape, can be longitudinally bent so as to adapt to the curvature of the bone, consequently enabling the screws to form an angle between them.

The advantages are readily apparent from the description.

The invention claimed is:

1. A method of fusing a joint, the method comprising:
spanning first and second bones separated by a joint with a bone plate, such that a first hole of the bone plate is aligned with a first bone of the joint and a second hole of the bone plate is aligned with a second bone of the joint;
inserting a first fixation member through the first hole of the plate and into the first bone of the joint;

inserting a second fixation member through the second hole of the plate and into the second bone of the joint; and inserting a third fixation member through a fixation pathway of the plate, into the first bone, across the joint, and into the second bone, wherein the fixation pathway extends from a top surface of the plate and towards the second bone, and wherein the fixation pathway is arranged at least partially through an extension, at least a portion of which is positioned below a bottom surface of the plate and between first and second sides of the plate, wherein the fixation pathway terminates at an exit hole, and insertion of the third fixation member through the fixation pathway results in the third fixation member extending through the exit hole, across the joint, and into the second bone.

2. The method of claim 1, wherein insertion of the third fixation member through the fixation pathway includes inserting the third fixation member from the top surface of the plate directly into the exit hole.

3. The method of claim 1, wherein the fixation pathway is spaced apart from the extension so as to form a gap between the pathway and the extension.

4. The method of claim 1, wherein the extension is angled by about between 30° and 60° with respect to a longitudinal axis of the plate.

5. The method of claim 1, further comprising forming a cavity in the first bone with a tool, and positioning the extension at least partially within the cavity.

6. The method of claim 1, wherein the extension extends from the bottom surface of the bone plate.

7. The method of claim 1, wherein the plate includes a plurality of holes arranged according to the corners of a triangle or of a quadrilateral, and the method further comprises inserting fixation members into each of the plurality of holes so that some of the fixation members extend into the first bone while some of the fixation members extend into the second bone.

8. The method of claim 7, wherein the plate is curved so as to adapt to the curvature of at least one of the first and second bones, and the method further comprises inserting a plurality of fixation members into the plurality of holes so that at least one of the plurality of fixation members is angled with respect to another of the plurality of fixation members.

9. The method of claim 1, wherein the first and second holes are locking holes.

10. The method of claim 9, wherein the first and second holes include threading for engaging with the first and second fixation members.

11. The method of claim 1, wherein the fixation pathway includes non-threaded interior walls.

12. The method of claim 1, further comprising the step of inserting a first temporary fixation pin into a first pin hole in the plate to temporarily affix the plate to bone.

13. The method of claim 12, further comprising the step of inserting a second temporary fixation pin into a second pin hole in the plate to temporarily affix the plate to bone.

14. The method of claim 13, further comprising the step of axially translating the second fixation pin within the second pin hole during compression of the first and second bones.

15. The method of claim 14, wherein the second pin hole is an elongate slot.

16. The method of claim 1, wherein the extension is a tab angled relative to a longitudinal axis of the plate.

17. A method of fusing together first and second bone parts, the method comprising:

forming a cavity in at least one of the first and second bone parts;

associating a bone plate with the first and second bone parts, such that the bone plate spans across the first and second bone parts and at least a first hole of the bone plate is aligned with the first bone part;

inserting a first fixation member through the first hole and into the first bone part;

positioning an extension of the plate at least partially within the cavity, the extension being recessed at least partially below a bottom surface of the plate; and inserting a second fixation member through a fixation pathway of the plate, into the first bone part, across a divide between the bone parts, and into the second bone part, the fixation pathway extending from a top surface of the plate downwards towards the extension, the fixation pathway being arranged at least partially through the extension, wherein the fixation pathway terminates at an exit hole, and insertion of the second fixation member through the fixation pathway results in the second fixation member extending through the exit hole, across the divide between the bone parts, and into the second bone.

18. The method of claim 17, wherein the bone plate includes holes for fixation members on either side of the extension.

19. The method of claim 17, wherein insertion of the second fixation member through the fixation pathway includes inserting the second fixation member from the top surface of the plate directly into the exit hole.

20. The method of claim 17, wherein the exit hole is formed through the extension.

21. The method of claim 20, wherein the fixation pathway includes non-threaded interior walls.

22. The method of claim 20, further comprising inserting a third fixation member through a third hole in the plate and into at least one of the first and second bone parts.

23. The method of claim 17, wherein the first and second bone parts are separated by a joint, and the method further comprises inserting a third fixation member through a third hole in the plate and into the second bone part.

24. The method of claim 23, wherein insertion of the second fixation member through the fixation pathway includes inserting the second fixation member across the joint.

25. The method of claim 17, wherein the first hole is a locking hole.

26. The method of claim 17, wherein a central axis of the second hole diverges from a central axis of the first hole.

27. The method of claim 26, further comprising associating a template of the bone plate with at least one of the first and second bone parts to determine the positioning of the extension.

28. The method of claim 27, wherein the template does not include an extension.

29. The method of claim 17, wherein the plate includes a set of pin holes adapted to receive temporary fixation pins, a first of the pin holes having an axis extending into the first bone part, and a second of the pin holes having an axis extending into the second bone part.

30. The method of claim 29, further comprising inserting first and second temporary fixation pins into each of the first and second pin holes, and axially translating the second fixation pin within the second pin hole during compression of the first and second bone parts.

31. The method of claim 20, wherein the extension is angled by about between 30° and 60° with respect to a longitudinal axis of the plate.

32. A method of fusing a joint, the method comprising:
spanning first and second bones separated by a joint with a bone plate, such that a first hole of the bone plate is aligned with a first bone of the joint and a second hole of the bone plate is aligned with a second bone of the joint;
inserting a first fixation member through the first hole of the plate and into the first bone of the joint;
inserting a second fixation member through the second hole of the plate and into the second bone of the joint; and
inserting a third fixation member through a third hole in the plate, into the first bone, across the joint, and into the second bone so that a free end of the third fixation member, not attached to any portion of the plate, resides in the second bone and a head of the third fixation member is seated in the third hole, the third hole being angled relative to a longitudinal axis of the plate through a thickness of the plate, wherein the third fixation member is the only fixation member extending across the joint.

33. The method of claim 32, wherein the third hole is angled by about between 30° and 60° with respect to the longitudinal axis of the plate.

34. The method of claim 32, wherein the first and second holes are locking holes.

35. The method of claim 34, wherein the first and second holes are threaded.

36. The method of claim 32, wherein the plate includes a plurality of holes arranged according to the corners of a triangle or of a quadrilateral, and the method further comprises inserting fixation members into each of the plurality of holes so that some of the fixation members extend into first bone while some of the fixation members extend into the second bone.

37. The method of claim 36, wherein the plate is curved so as to adapt to the curvature of at least one of the first and second bones, and the method further comprises inserting a plurality of fixation members into the plurality of holes so that at least one of the plurality of fixation members is angled with respect to another of the plurality of fixation members.

38. The method of claim 37, further comprising the step of inserting a temporary fixation pin into a hole in the plate to temporarily affix the plate to bone.

39. The method of claim 32, wherein the joint is one of the anatomical joints of the human body in the foot or hand.

40. The method of claim 1, wherein the joint is one of the anatomical joints of the human body in the foot or hand.

\* \* \* \* \*